United States Patent
Fuchita et al.

(10) Patent No.: US 7,483,737 B2
(45) Date of Patent: Jan. 27, 2009

(54) ELECTRODE CHIP FOR BIOLOGICAL APPLICATION AND ITS USING METHOD

(75) Inventors: Yasushi Fuchita, Tokyo (JP); Tatsuya Ogawa, Tokyo (JP); Saori Takahashi, Tokyo (JP); Mitsuru Kuribayashi, Tsukuba (JP); Naruhito Higo, Tsukuba (JP)

(73) Assignee: Hisamitsu Pharmaceutical Co., Inc, Saga (JP)

( * ) Notice: Subject to any disclaimer, the term of this patent is extended or adjusted under 35 U.S.C. 154(b) by 303 days.

(21) Appl. No.: 10/579,287

(22) PCT Filed: Oct. 22, 2004

(86) PCT No.: PCT/JP2004/015697

§ 371 (c)(1), (2), (4) Date: May 15, 2006

(87) PCT Pub. No.: WO2005/049133

PCT Pub. Date: Jun. 2, 2005

(65) Prior Publication Data

US 2007/0129664 A1    Jun. 7, 2007

(30) Foreign Application Priority Data

Nov. 18, 2003  (JP) .............................. 2003-387509

(51) Int. Cl.
*A61N 1/30* (2006.01)
(52) U.S. Cl. ............................................ 604/20
(58) Field of Classification Search ............. 604/19–22, 604/65–67; 128/DIG. 12, DIG. 13
See application file for complete search history.

(56) References Cited

FOREIGN PATENT DOCUMENTS

| | | |
|---|---|---|
| EP | 1 177 814 A | 2/2002 |
| JP | 2000-316991 A | 11/2000 |
| WO | WO 00/69515 | 11/2000 |

*Primary Examiner*—Manuel A Mendez
(74) *Attorney, Agent, or Firm*—Frommer Lawrence & Haug, LLP; Ronald R. Santucci

(57) ABSTRACT

This invention relates to a technology for preventing leakage of liquid from gel (70). The electrode chip (10) comprises a cup-like support (20) including a cup part (210), and a sheet-like support (30) attached with an electrode layer (40). The gel (70) in the cup part (210) delivers liquid (700) containing water confined at the time of crosslinking. The liquid (700) moves by capillarity from the gel (70) side through a narrow gap between the outer flange (220) of the cup-like support (20) and the outside part (310*o*) of the sheet-like support (30) in a direction away from the gel (70). Since a groove (80) exists in the vicinity of the cup part (210) and the gap is large at that part, capillarity is broken thereat.

10 Claims, 2 Drawing Sheets

US 7,483,737 B2

ELECTRODE CHIP FOR BIOLOGICAL APPLICATION AND ITS USING METHOD

This application is a 371 of PCT/JP2004/015697 filed on Oct. 22, 2004, published on Jun. 2, 2005 under publication number WO 2005/049133 A which claims priority benefits from Japanese Patent Application Number 2003-387509 filed Nov. 18, 2003.

TECHNICAL FIELD

This invention relates to an electrode chip or device for biological application which can be used in the medical field of treatment and diagnosis of diseases, and more particularly to an electrode device capable of preventing a medicine and a physiologically active ingredient from leaking.

BACKGROUND ART

Iontophoresis (Acta Dermatol Venereol, vol. 64, p. 93, 1984) and electroporation (domestic republication No. H-03-502416 of PCT international application, Proc. Acad. Sci. USA, vol. 90, pp. 10504 to 10508, 1993) teach a treatment method for introducing a medicine and a physiologically active ingredient into a living body through skin or mucous membrane using electrical energy. There is also known a method for observing the patient's condition by taking out a diagnosing substance from a living body using the same principle as just mentioned above (Nature Medicine vol. 1, pp. 1198 to 1201, 1995). In those methods, an electrode device is necessarily used for applying an electrical energy.

Patent Document 1: Japanese Patent Application Laid-Open No. 2000-316991

Patent Document 1 discloses an idea for making an electrode device of this type disposable while an external power supply such is designed as to be used repeatedly. The disposable electrode device includes an electrode part at its bottom part and a support provided with a recess which is open upward. A medicine holding layer containing and holding a medicine, etc. therein is arranged in the recess. The recess with the medicine holding layer arranged therein is hermetically covered at an upper part thereof with a cover member. For use, the cover member is peeled off so that the medicine holding layer can contact the living body. The cover member is bonded to a flange part of the support and the recess is hermetically sealed.

In the electrode device of this type, the holding ability of the medicine holding layer can be increased with respect to the support since the medicine holding layer containing and holding a medicine, etc. therein (namely, medicine holding layer containing an electrolyte) is put into the recess. In actual practice, however, it is difficult to contact the entire upper surface of the medicine holding layer with the living body closely (the problem of contacting with the living body). It is because the top part of the medicine holding layer in the recess is generally flat with the height of the opening part of the recess.

Moreover, the support for supporting the medicine holding layer includes an electrode layer adapted to apply an electrical energy to the medicine holding layer. This electrode layer extends from inside the recess to outside the recess. The support for supporting the medicine holding layer and the cup covering an upper part thereof are, in general, joined by heat sealing or bonding. For use, the cup is peeled off the support.

At the time of peeling off the cup from the support, the electrode layer is frequently subjected to damage (the problem of damage given to the electrode layer).

DISCLOSURE OF THE INVENTION

Problems to be Solved by the Invention

The inventors tried to develop an electrode device of a new type taking into consideration the above-mentioned problems, i.e., the problem of contacting with the living body and the problem of damage given to the living body). In the new type electrode device, firstly, in order to achieve the intimate contact to the living body, it was designed such that the medicine holding layer projects from the surface of the support at the time of application to the living body. In one embodiment, instead of supporting the medicine holding layer on the side of the support having the recess, the medicine holding layer is supported on the side of the other support which covers the opening part of the recess. Different from the cup-like support having the recess, the other support is normally in the shape of a sheet and flat. Owing to this feature, the medicine holding layer supported on the sheet-like support is greatly projected from the surface of the support and the entire upper surface can effectively intimately be contacted with the living body (FIG. 1A). In another embodiment, the medicine holding layer is supported in the recess at the side of the cup-like support as in the conventional manner and another recess (this recess is less deep than the recess of the cup-like support) is also formed in the other support. Owing to this arrangement, the medicine holding layer projects from the recess by a portion equal to the depth of the less deep recess on the cup-like support (FIG. 1B).

In the new electrode device, secondly, in order to prevent the damage given to the electrode layer, at least a certain place of the electrode layer is left in a non-joined state contrary to the conventional manner.

However, it became clear that a new problem arises in case the medicine holding layer is projected from the surface of the support and at least a part of the mutually superimposing two supports is left in a non-joined state. The new problem is that liquid leakage tends to occur from the medicine holding layer. The leakage of liquid creates a problem not only during the process for manufacturing an electrode device of this type but also in the process of storing the device as a product after it is manufactured. For example, during the manufacturing process, a low viscous content tends to leak from the cup-like molding part (cup part) and this leakage degrades the manufacturing efficiency in the succeeding processes (sealing process and packaging process). The leakage occurrable during the manufacturing process is chiefly attributable to physical pressure, capillarity and the like. The leakage is, in some case, attributable to bleeding from the medicine holding layer. It seems that water or the like confined in a three-dimensional structure of a gel molecule of the medicine holding layer flows out. With respect to this bleeding, especially, in case the gel is crosslinked in order to improve the shape retention after the gel having a comparatively high flowability is filled in the recess (a closed space defined by the cup-like support and the sheet-like support), a liquid comes out in accordance with the progress of crosslink. The liquid coming out of the gel leaks in such a manner as to ooze out of a gap between the cup-like support and the sheet-like support by capillarity. From the view point that the volume of the gel is set to be a specified capacity and the effect of the medicine is uniformized, such leakage is not favorable. It is, therefore, demanded the such leakage is effectively prevented from occurring. The specified capacity of the medicine holding layer containing a form of gel requires such a high precision as about 1/100 cc.

The present invention has been accomplished in view of the above-mentioned various points. It is, therefore, an object of the invention to provide an electrode device or chip having such a form of support that a medicine holding layer projects from one surface of a support, capable of effectively preventing leakage of a liquid from the medicine holding layer from occurring.

It is another object of the present invention to provide an electrode device capable of effectively preventing leakage of a liquid from a medicine holding layer irrespective of the fact that at least a part of a mutually superimposing part between a cup-like support and a sheet-like support is in a non-joined state.

A further object of the present invention is to provide a method for effectively using such an electrode device as mentioned above.

Other objects of the present invention will become more manifest from the following description.

Means for Solving the Problems

According to the present invention, a medicine holding layer is supported in such a manner that the medicine holding layer projects from a surface of a support contrary to the conventional manner in which a medicine holding layer fully filled in a recess is contacted with a living body. As a form of support in which a medicine holding layer projects from the surface of a support, there are various forms as mentioned above. More preferably, a medicine holding layer projecting from the surface of a support is supported on a sheet-like support which is flat or slightly recessed. Firstly, owing to the foregoing arrangement, the surface of the medicine holding layer and the living body are reliably contacted with each other. To this end, the sheet-like support for supporting the medicine holding layer includes an electrode layer adapted to apply an electrical energy to the medicine holding layer.

The sheet-like support defines a chamber for receiving therein the medicine holding layer, together with a cup-like support including a cup part which defines a recess. In the two supports which define a chamber, an outer flange (the flange of the cup-like support) surrounding the outer periphery of the recess over one circumference thereof and an outer part (the outer part corresponding to the flange of the sheet-like support) surrounding the outer periphery of the inner part, where the medicine holding support is arranged, over one circumference thereof are surface contacted with each other. The expression "surface contacted" herein used refers not to a state wherein a completely hermetically sealed state as in the heat sealing is obtained as in the conventional case but to a state wherein a small gap is formed so that capillarity works at the surface contacting part. In this respect, according to the present invention, the sheet-like support and the cup-like support are temporarily superimposed with each other and are not positively sealed at the contact surfaces by heat sealing or the like contrarily to the conventional case. The expression "temporarily" refers not only to the temporary interval, for example, from the time the medicine holding layer of the form of gel is crosslinked to the time the cup-like support is removed therefrom but also to the temporary time from the time the product is stored to the time the cup-like support is removed therefrom so as to be made ready for use.

Also, according to the present invention, in order to prevent damage given to the electrode layer, at least a place where the electrode layer is located is left in a non-joined state. To this end, the electrode device according to the present invention comprises a leakage prevention means for preventing the liquid from flowing out of the medicine holding layer located inside the mutually superimposing outer flange and outer part through a gap (namely, the gap formed between the outer flange and the outer part at the non-joining part).

As the leakage prevention means, several types are applicable. In the first type, at least one of the mutually superimposing outer flange and outer part is accompanied with a physical shape deformation, and in the second type, a surface chemical is accompanied without being accompanied with such a physical shape deformation.

In the latter second type, the respective surfaces of the mutually confronting parts of the outer flange of the cup-like support and the outer part of the sheet-like support are specified in surface characteristics. In this means, a contact angle with the water is set to be 90 degrees or more. As such means (namely, the second type leakage prevention means), there are a method in which a surface coating layer containing a water repellent material is provided, a method for forming the support with a resin having a high water repellency and another water repellent treatment. As such a water repellent material, there can be listed fluorized materials (ethylene tetrafluoride, poly perfluorooctyl ethyl acrylate, ethylene tetrafluoride/perfluorovinyl ether copolymer, ethylene tetrafluoride/propylene hexafluoride copolymer, ethylene/ethylene tetrafluoride copolymer, poly-vinylidene fluoride, trifluoro ethylene chloride resin, etc.), siliconized materials (dimethyl silicone, poly methyl hydrogen siloxane, methylphenyl silicone, dimethyl silicone, poly dimethyl siloxane, etc.), poly methyl pentene, paraffin, polyethylene, etc. They can be used either alone or in combination. They may also be copolymerized or modified for use. Those water repellent materials themselves are known per se and many of them are commercially available. Specific examples of commercially available products are, for example, there can be listed Modiper F (fluorized materials) and Modiper FS (siliconized materials) of NOF Corp., TPX (poly methyl pentene) of Mitsui Chemicals, Inc., Unidyne, Zeffle, Neoflon (fluorized materials) of Daikin Ind. Ltd., and oil, resin and rubber (siliconized materials) of Shinetsu Silicone. By using them alone or by kneading or coating them with other materials, an intended water repellency can be obtained. Since the medicine holding layer can easily be peeled off the cup by using the water repellent material, the feel of use is good.

Even in case the second type is used alone, the liquid can be prevented from leaking. More preferably, however, the second type is used in combination with the first type in which physical shape deformation is accompanied. By using the mutually different type of leakage prevention means in combination, leakage can more reliably be prevented from occurring and physical shape deformation can relatively be lessened. More specifically, in the second type using a water repellent material, when an external physical pressure is exerted to the medicine holding layer, it is rather difficult to reliably prevent the liquid from leaking. In this respect, in the first type in which physical shape deformation is accompanied, leakage can more reliably be prevented even in such a case. Thus, it is most suitable to use the first and second types in combination.

The shape deformation in the first type has such a technical significance that by enlarging the gap between the mutually superimposing parts than that between the rest parts, leakage attributable to liquid, particularly leakage attributable to surface tension (or capillarity) can be prevented from occurring.

The size of the gap is thought to be in inverse proportion to easiness in oozing (height or distance of oozing). Accordingly, if the gap is such designed as to have a predetermined size or more, the liquid can be prevented from oozing out of the gap. The leakage prevention means in the first type is based on such an idea. That is, the part where the medicine holding layer is filled is provided at the outer periphery (preferably, a proximate part as much as possible) with a shape deformation part capable of more enlarging the gap than the gap formed between the rest parts. This shape deformation part may be provided to one or both of the two supports which are in surface contact with each other. Preferably, the shape deformation part is provided on the side of the cup-like support which defines the recess in such a manner as to surround the outer periphery of the recess. As the shape deformation part, the ring-like recess is most suitable. Such a groove can simultaneously be obtained at the time the recess is shaped. Since the groove is adapted to more enlarge the gap than the gap between the rest parts, it has the same depth direction as the recess. The depth dimension (d) of the groove is preferably a value which satisfies the expression $0.1 \text{ mm} \leqq d \leqq a$ depth of the recess (for example, 2 mm). The value of 0.1 mm is a lowermost value taking into consideration of leakage prevention and easiness of working. While the uppermost value of the recess is the value taking into consideration of limitation in shaping.

In view of one mode of use of the present invention, according to the invention, after gel (in other words, the medicine holding layer in the form of gel) as a medicine holding layer is filled in the chamber defined by the two supports, the gel is crosslinked in order to improve the shape retention and thereafter, the cup-like support is removed from the sheet-like support while keep remaining the gel on the side of the sheet-like support. Then, the upper surface of the gel projecting upward of the sheet sheet-like support is contacted with skin of the living body or the like and an electrical energy is applied to the gel through an electrode layer. Accordingly, from the viewpoint that the medicine holding layer in the form of gel is more reliably supported, it is preferable that a support surface on the side of the sheet-like support is matted so that it has a proper surface roughness. In this respect, since the electrode layer contains fine particles such as silver chloride and silver, it inherently has a proper surface roughness for holding a medicine holding layer which is in the form of gel. In contrast, the surface roughness of a plastic sheet material as the main body of the sheet-like support is very small. In order to increase the supporting force of the electrode layer and/or increase the supporting force of the gel expanding from the area of the electrode layer, the surface of the plastic sheet material may be preliminarily matted.

As the medicine holding layer, there are two types; an impregnating type wherein a medical solution is impregnated in an impregnating material and a matrix type wherein a medicine is held in its gel-like or semi-solid state having a shape retention. In the impregnating type, a low viscous medical solution is held in a sponge, a porous material or the like such as non-woven fabric, absorbent cotton, gauze, paper, synthetic resin open cell foam or absorbent resin and stored in that condition. Such an impregnating type base material is laminated on the electrode layer by working means. On the other hand, in the matrix type, it is preferable that a hydrophilic base material is used, for example, an ionic synthetic polymer such as polyacrylic acid, partially neutralized salt of polyacrylic acid, perfectly neutralized salt of polyacrylic acid, a copolymer and neutralized salt of methoxyethylene/maleic acid anhydride, a copolymer and neutralized salt of methoxyethylene/maleic acid, carboxyvinyl polymer, starch polyacrylate, polyacrylic amide and polyacrylic amide derivative, a copolymer of N-vinyl acetoamide/acrylic acid and acrylate, a nonionic synthetic copolymer such as polyvinyl alcohol, polyvinyl pirrolidone, polyethylene oxide, and a natural resin and a semi-synthetic resin such as arabic gum, tragacanth gum, locust bean gum, gua gum, ecco gum, karaya gum, agar, starch, carrageenan, alginic acid, alginate, propylene glycol alginate, dextran, dextrin, amylose, gelatin, collagen, pullulan, pectin, amylopectin, starch, chitin, chitosan, albumin, casein, methylcellulose, ethylcellulose, propylcellulose, ethymethylcellulose, hydroxy methylcellulose, hydroxy ethylcellulose, hydroxy propylmethylcellulose, and hydroxypropyl starch. They are added with water so as to become a gel state or solid state. Moreover, they are added with glycols such as glycerin, ethylene glycol, diethylene glycol, triethylene glycol, polyethylene glycol, propylene glycol, and polypropylene glycol, diols such as 1,3-propane diol, and 1,4-butane diol, and sugar alcohols such as D-sorbitol, xylitol, manitol, and erythritol so that they are plasticized to be made into a semi-solid gel or ointment or in the shape of gel having a self shape retention by crosslink (in other words, the form of gel). The matrix type base material which is applied in the present invention has such rheology that flowability is high during the manufacturing process and problematical in manufacturing suitability. In some cases, bleeding of the component occurs with the passage of time during storage.

DESCRIPTION OF REFERENCE NUMERAL

Figure 1A:
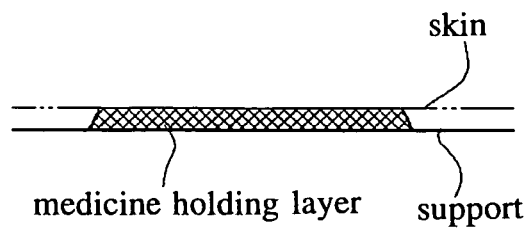
FIG. 1A is a schematic view showing one mode of support according to the present invention.
Figure 1B:
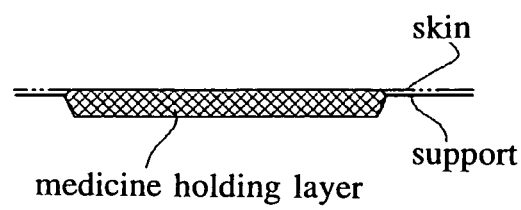
FIG. 1B is a schematic view showing another mode of support according to the present invention.

10 . . . electrode device (electrode chip)
20 . . . cup-like support
210 . . . cup part
220 . . . outer flange
22 . . . recess
30 . . . sheet-like support
300 . . . base sheet
40 . . . electrode layer
50 . . . chamber
70 . . . medicine holding layer (gel)
80 . . . groove (shape deformation part)

BEST MODE FOR CARRYING OUT THE INVENTION

As apparent from the foregoing, the most preferred mode comprises a first type leakage prevention means in which a shape deformation is accompanied, and a second type leakage prevention means in which a shape deformation is not accompanied.

Figure 2:
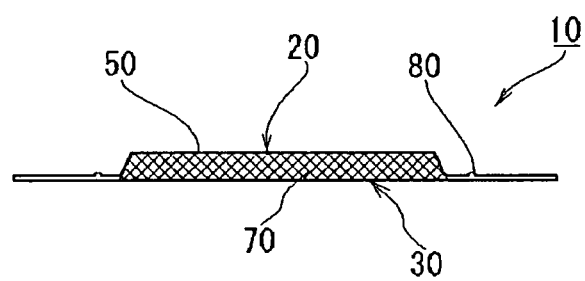
FIG. 2 is a construction view, in section, showing one preferred embodiment of the present invention.

FIG. 2 shows an entire construction of an electrode device 10 according to a first embodiment of the present invention. The electrode device 10 comprises a cup-like support 20 and a sheet-like support 30 superimposed therewith. Both the supports 20, 30 define therebetween a chamber 50 for filling therein a gel (namely, medicine holding layer) containing an electrolyte.

Figure 3:
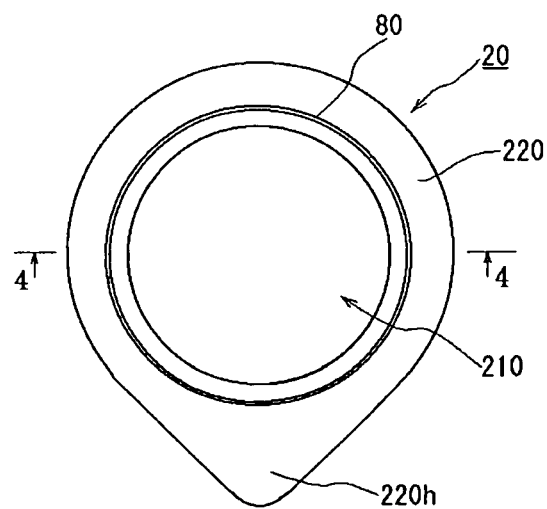
FIG. 3 is a plan view of a cup-like support which the device of FIG. 2 has.
Figure 4:
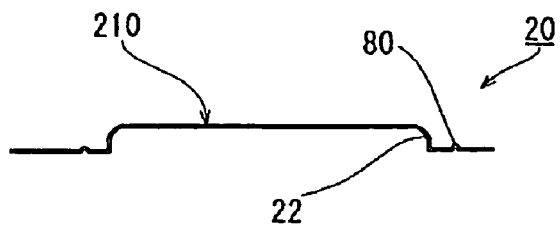
FIG. 4 is a sectional view taken on line 4-4 of FIG. 3.

FIGS. 3 and 4 show the cup-like support 20 more specifically. The cup-like support 20 is a product molded from plastic. The cup-like support 20 integrally includes a cup part 210 defining a recess 22 and an outer flange 220 surrounding the outer periphery of the cup part 210 over one circumference. The cup-like support 20 can basically be composed of various plastic material, or metal material such as aluminum. In view of working, plastic material is preferable and it is more preferable to use water-repellent material as in an example which will be described later. In case of plastic material, its thickness is, for example, about 0.2 mm. The recess 22 is, for example, about 2 mm in depth and about 20 to 30 mm in inside diameter. The outer flange 220 around the cup part 210 is about 10 mm in width. The outer flange 220 has a triangular handle part 220*h* projecting from a part thereof.

Figure 5:
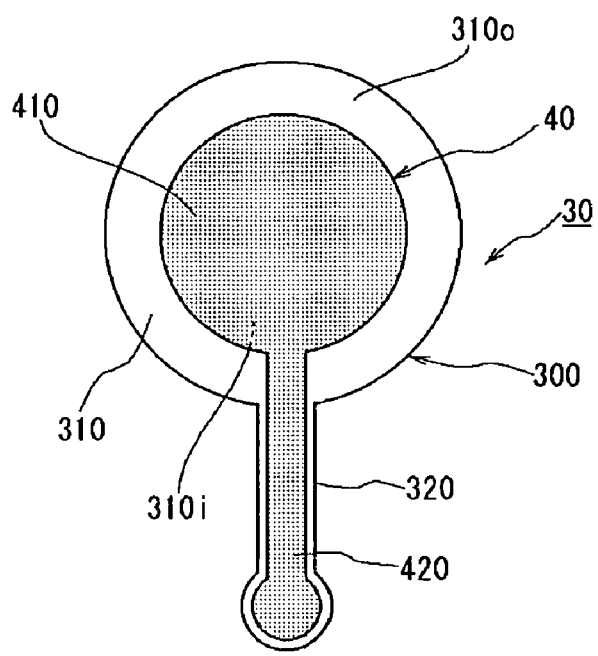
FIG. 5 is a plan view of a sheet-like support which the device of FIG. 2 has.

FIG. 5 is a view of the cup-like support 30 when viewed from above. The sheet-like support 30 comprises a base sheet 300 made of plastic sheet material and an electrode layer 40 laminated on the base sheet 300. The base sheet 300 of the sheet-like support 30 includes a circular main body part 310 and a lead part 320 linearly extending from the main body part 310. The circular main body part 310 has an inner part 310*i* corresponding to the cup part 210 of the cup-like support 20 and an outer part 310*o* (part corresponding to the outer flange part 220 of the cup-like support 20) surrounding the outer periphery of the inner part 310*i* over one circumference. The electrode layer 40 located on the base sheet 300 likewise includes a circular electrode main body 410 and an electrode lead part 420 linearly extending from the electrode main body 410. The material of the base sheet 300 should be selected from those which are excellent in electrically insulating property. For example, flexible (for example, about 70 to 80 μm in thickness) white polyethylene terephthalate (PET) is preferable. More preferably, its surface is matted by sand blast or the like. The electrode layer 40 can be formed by screen printing using conductive paste ink. The material of conductive paste ink is selected from those whose main component is, for example, silver, silver chloride and carbon. Particularly, silver is preferable an electrode component used as an anodic electrode and silver chloride containing silver is preferable on the cathodic electrode side because no polarization occurs. An insulating layer, as later described, is formed on the outer peripheral part of the main body part 310 surrounding the circular main body part 410.

There are mostly two methods for filling a gel 70 in the chamber 50 between the cup-like support 20 and the sheet-like support 30. In the first method, the gel 70 is filled in the recess 22 of the cup-like part 210 of the cup-like support 20 by a metering pump and thereafter, the sheet-like support 30 is placed on the recess 22 in order to cover the recess 22. Then, heating is applied to the gel 70 for crosslink and then, the device is subjected to packaging. In the second method, after the gel 70 is placed on the circular electrode main body 410 of the sheet-like support 30 by a metering pump, the cup-like support 20 is placed thereon for coverage, and then, after the gel 70 is crosslinked, the device is subjected to packaging.

When such methods are carried out, the problem of leakage of liquid coming out of the gel 70 occurs as previously mentioned. In order to solve the problem of leakage, according to the present invention, firstly, a shape deformation part is provided to at least one of the outer flange 220 of the cup-like support 20 and the outer part 310*o* of the sheet-like support 30 which are superimposed with each other. Owing to this arrangement, a part of a gap formed therebetween is more enlarged than that between the rest parts. That is, as one example of such a shape deformation part, a groove 80 surrounding the outer flange 220 of the cup-like support 20 is provided to a place proximate to the cup-like part 210 (see FIGS. 2 through 4 and 6). The groove 80 is about 0.1 mm to 2 mm, preferably about 0.2 mm to 0.3 mm in depth and about 1 mm in width. The groove 80 itself can be made together with the recess part 22 simultaneously when the cup-like support 20 is molded (for example, vacuum molding, vacuum air-pressure molding, press molding, injection molding, etc.).

Figure 6:
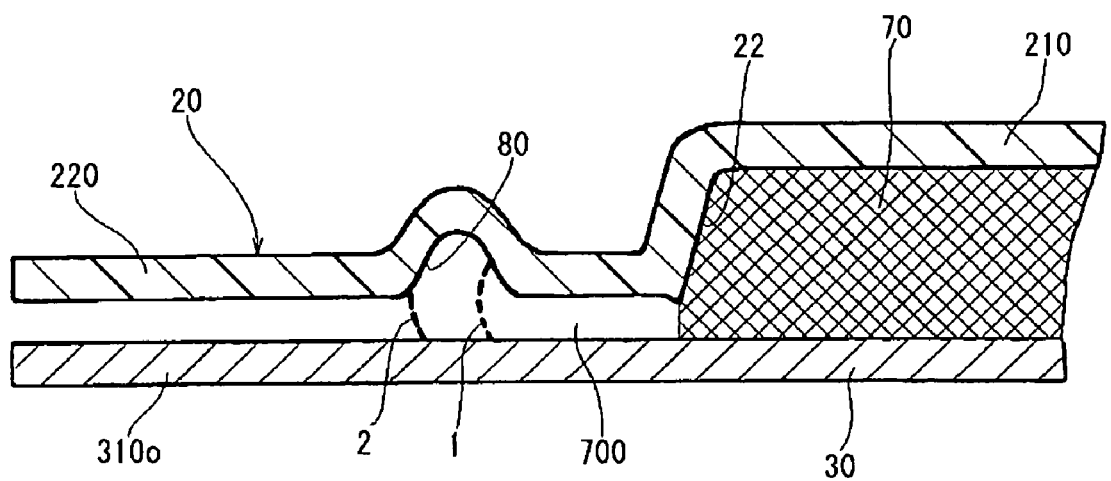
FIG. 6 is a partly enlarged view showing the function for preventing leakage.

FIG. 6 shows the function of the groove 80 which is the shape deformation part. The gel 70 in the cup part 21 spills a liquid 700 containing water, etc. Confined therein when the gel 70 is crosslinked. This liquid 700 is moved from the side of the gel 70 in a direction away from the gel 70 through a small gap between the outer flange 220 of the cup-like support 20 and the outer part 310*o* of the sheet-like support 30 by capillarity. However, since the groove 80 is located near the cup part 210 and the gap at that part is larger than the gap between the peripheral parts adjacent thereto, capillarity is broken. Thus, the liquid 700 is stopped at the groove 80 either in the manner 1 or manner 2 indicated by broken lines. Therefore, the liquid 700 does not flow out over the groove 80 and excessive leakage of the liquid 700 can thus be prevented from occurring.

As described hereinbefore, the electrode device 10 according to one embodiment of the present invention provides a new mode for supporting the gel 70 which is a medicine holding layer on the flat sheet-like support 30. At the time of use of the electrode device 10, the cup-like support 20 is removed from the sheet-like support 30 by using the handle part 220*h* of the cup-like support 20. The gel 70 remained on the sheet-like support 30 is in an attitude projecting from the surface of the sheet-like support 30. Therefore, when the gel 70 remained on the sheet-like support 30 is placed on the skin of a living body, or the like, the surface of the gel 70 is reliably contacted with the living body.

In addition to a provision of the groove 80 (first type leakage prevention means) which is a shape deformation part, the electrode device 10 is further provided with a second leakage prevention means for water repellency. Specific examples of the second leakage prevention means will be described hereinafter.

EXAMPLE 1

An electrode layer 40 was formed on a single surface of a base sheet (PET) 300 by screen printing using conductive silver paste ink. Then, by applying a paste ink composed of polyester resin added with silicone oil (KS-69 of Shinetsu Silicone) along the outer periphery of the circular part 410 of the electrode layer 40 through screen printing, an insulating layer was formed on an outer peripheral part of the main body part 310 surrounding the circular electrode main body 410. On the other hand, a cup-like support 20 having an opening diameter of 30 mm, a width of 10 mm and a height of 2 mm at the outer flange 220 was obtained by vacuum molding.

EXAMPLE 2

An insulating layer was formed on an outer peripheral part of the main body part 310 surrounding the circular electrode main body 410 of the sheet-like support 30 in the same manner as in Example (1). Instead of the polypropylene sheet, a PET sheet with silicon resin coated thereon was used as a material for molding the cup-like support 20.

EXAMPLE 3

The insulating layer in Example 1 was formed by laminating a film of polymethyl penten instead of screen printing. Similarly, the cup-like support 20 was manufactured by injection molding using resin of polymethyl penten.

EXAMPLE 4

The insulating layer in Example 1 was formed by printing using ink composed of fluorine-based resin (Modiper F). Similarly, the cup-like support 20 was manufactured by injection molding using fluorine-based resin (Neoflon PFA).

EXAMPLE 5

The insulating layer in Example 1 was formed by printing using ink composed of silicone-based resin (Modiper FS). Similarly, the cup-like support 20 was manufactured by injection molding using silicone rubber (BY-LSR2030 of GE Toshiba Silicone)

EXAMPLE 6

An electrode layer 40 was formed on a single surface of the base sheet (PET/aluminum/PET) 300 by screen printing using a conductive silver paste ink. An insulating layer was formed on an outer peripheral part of the main body part 310 surrounding the circular electrode main body 410 by screen printing along the outer periphery of the circular part 410 of the electrode layer 40 using paste ink composed of polyether resin added with silicone oil (KS-69 of Shinetsu Silicone). By applying cold press working and punch press working to the base sheet containing the electrode layer 40, a cup-like support was formed.

EXAMPLE 7

A sheet-like support 30 containing an insulating layer was made in the same manner as in Example 1. Similarly, a cup-like support 20 was manufactured by vacuum molding using a polypropylene sheet with silicone resin coated on its surface basically in the same manner as in Example 1. In this Example, however, different from Example 1, a recess (namely, shape deformation part) having a width of 1 mm and a depth of 0.2 mm was additionally formed on the outer peripheral part of the opening part of the cup-like support 20.

COMPARATIVE EXAMPLE

An electrode layer was formed on a single surface of a base sheet (PET) by screen printing using conductive silver paste ink. Also, a cup-like support having an opening diameter of 30 mm, a width of 10 mm and a height of 2 mm at the outer flange was obtained by vacuum molding using PET.

A medicine holding layer (gel) was filled in the cup-like support in the specific examples (Examples 1 to 7) and the Comparative Example, a sheet-like support containing an electrode layer was put thereon and leakage of a solvent (water) was observed. Moreover, after the gel was crosslinked, the cup-like support was peeled off and the peel-off condition and the sense of peel-off were evaluated. As a result, leakage of a liquid was observed in the Comparative Example but no leakage was observed in the respective Examples 1 to 7. Moreover, in Comparative Example, the gel was adhered to the cup-like support too hard to peel off and the sense of peel-off was heavy but in the respective Examples 1 to 7, the gel was not adhered to the support, the sense of peel-off was light and peel-off was easy.

The invention claimed is:

1. An electrode device comprising:
   a cup-like support integrally including a cup part defining a recess and an outer flange surrounding an outer periphery of said cup part over a circumference thereof; and
   a sheet-like support integrally including an inner part having an area corresponding to said cup-like part and an outer part surrounding an outer periphery of said inner part over a circumference thereof,
   said cup-like support and said sheet-like support being designed such that said outer flange and said outer part are superimposed with each other in such a manner as to be surface contacted with each other, thereby defining a chamber for receiving a medicine holding layer containing an electrolyte at said cup part that is located on an inner side, one of said cup-like support and said sheet-like support being provided with an electrode layer extending from inside said chamber to outside said chamber,
   said electrode device comprising the following respective features;
   A. at least a place, where said electrode layer is formed, of the superimposing part between said outer flange of said cup-like support and the outer part of said sheet-like support, wherein said place is in a non-joined state, and
   B. at least one of said outer flange and said outer part which are superimposed with each other is provided with a leakage prevention means in order to prevent a liquid, which flows out of said medicine holding layer loaded in said chamber, from leaking through a gap occurrable at said place in said non-joined state.

2. An electrode device according to claim 1, wherein said liquid leakage prevention means is a shape deformation part disposed at least at one of said mutually superimposed outer flange and outer part and the gap between said mutually superimposing parts is more enlarged than that between the rest parts by said shape deformation part, thereby eliminating the leakage attributable to said liquid.

3. An electrode device according to claim 2, wherein said shape deformation part is located on the side of said cup-like support including said cup part.

4. An electrode device according to claim 3, wherein said shape deformation part is a ring-like groove formed in said outer flange and a depth direction of said groove is same as that of said recess of said cup part.

5. An electrode device according to claim 4, wherein the depth d of said groove satisfies 0.1 mm$\leq$d$\leq$depth of said recess.

6. An electrode device according to claim 1, wherein said liquid leakage prevention means specifies surface characteristics of the respective surfaces of the mutually confronting places of said outer flange of said cup-like support and said outer part of said sheet-like support, and a contact angle with water is set to be 90 degrees or higher.

7. An electrode device according to claim 6, wherein the respective surfaces of said mutually confronting surfaces of said outer flange of said cup-like support and said outer part of said sheet-like support are each provided with a surface coating layer containing a water repellent material.

8. An electrode device according to claim 1, wherein said liquid leakage prevention means is composed of a combination of two mutually different means and comprises first means which is said shape deformation part disposed at least at one of said outer flange and said outer part which are superimposed with each other, a gap between said superimposing parts being more enlarged than that between the rest parts by said shape deformation part so that leakage attributable to said liquid can be eliminated, and second means specifying the surface characteristics of the respective surfaces of the mutually confronting places of said outer flange of said cup-like support and said outer part of said sheet-like support, in which the contact angle with water is set to be 90 degrees or higher.

9. An electrode device according to claim 1, wherein said sheet-like support is a plastic sheet material whose surface is matted, said electrode layer is supported by the matted surface of said plastic sheet material, a gel, that is said medicine holding layer, is placed on said electrode layer and an outer peripheral part of said gel is placed on the surface of said matted plastic sheet material.

10. A method of using an electrode device comprising a cup-like support integrally including a cup part defining a recess and an outer flange surrounding an outer periphery of said cup part over a circumference thereof; and a sheet-like support integrally including an inner part having an area corresponding to said cup-like part and an outer part surrounding an outer periphery of said inner part over a circumference thereof, said cup-like support and said sheet-like support being designed such that said outer flange and said outer part are superimposed with each other in such a manner as to be surface contacted with each other, thereby defining a chamber for receiving a medicine holding layer containing an electrolyte at said cup part that is located on an inner side, one of said cup-like support and said sheet-like support being provided with an electrode layer extending from inside said chamber to outside said chamber, said electrode device comprising the following respective features;

A. at least a place, where said electrode layer is formed, of the superimposing part between said outer flange of said cup-like support and the outer part of said sheet-like support is in a non-joined state, and B. at least one of said outer flange and said outer part which are superimposed with each other is provided with a leakage prevention means in order to prevent a liquid, which flows out of said medicine holding layer loaded in said chamber, from leaking through a gap occurrable at said place in said non-joined state, said method comprising, at the time of using said electrode device, filling a gel as said medicine holding layer in said chamber and then said gel is crosslinked to more enhance the shape retainability than before said gel is filled in said chamber and thereafter removing said cup-like support from the side of said sheet-like support while remaining said gel on the side of said sheet-like support.

* * * * *